United States Patent
Bequette

(10) Patent No.: US 10,191,036 B1
(45) Date of Patent: Jan. 29, 2019

(54) SYSTEM FOR DETECTING AND REMOVING BIOLOGICAL ANALYTES IN FLUIDS

(71) Applicant: John B. Bequette, Huntsville, AL (US)

(72) Inventor: John B. Bequette, Huntsville, AL (US)

(73) Assignee: NUB4U, Inc., Huntsville, AL (US)

( * ) Notice: Subject to any disclaimer, the term of this patent is extended or adjusted under 35 U.S.C. 154(b) by 0 days.

(21) Appl. No.: 15/928,208

(22) Filed: Mar. 22, 2018

(51) Int. Cl.
| | |
|---|---|
| *B01D 15/10* | (2006.01) |
| *C02F 1/28* | (2006.01) |
| *G01N 33/18* | (2006.01) |
| *G01N 33/28* | (2006.01) |
| *G01N 33/53* | (2006.01) |

(Continued)

(52) U.S. Cl.
CPC ............ *G01N 33/53* (2013.01); *B01D 15/10* (2013.01); *C02F 1/285* (2013.01); *G01N 33/1826* (2013.01); *G01N 33/2835* (2013.01); *G01N 33/56911* (2013.01); *G01N 33/56983* (2013.01); *G01N 33/573* (2013.01); *C02F 2209/006* (2013.01); *C02F 2209/008* (2013.01); *C02F 2303/04* (2013.01)

(58) Field of Classification Search
CPC ............ G01N 1/28; G01N 1/40; G01N 1/405; G01N 27/02; G01N 27/021; G01N 27/26; G01N 27/28; G01N 27/30; G01N 27/301; G01N 27/327; G01N 27/3275; G01N 27/3278; G01N 27/42; G01N 33/1826; G01N 33/26; G01N 33/28; G01N 33/2835; G01N 33/53; G01N 33/569; G01N 33/56911; G01N 33/56916; G01N 33/56983; G01N 33/573; G01N 2201/2826; G01N 2035/1053; G01N 2333/005; G01N 2333/195; G01N 2333/265; G01N 2333/38; G01N 2333/40; C02F 1/285; C02F 2209/008; C02F 2303/04; C02F 2209/006; C02F 1/004; C02F 1/008; C02F 1/28; C02F 1/286; C02F 1/288; C02F 2101/30; C02F 2209/36; B01D 15/10; B01D 24/02; B01D 24/002; B01D 24/007; B01D 2215/00

USPC ...... 204/400, 403.1, 406, 409; 210/85, 96.1, 210/739, 746; 340/603; 436/177

See application file for complete search history.

(56) References Cited

U.S. PATENT DOCUMENTS

| | | |
|---|---|---|
| 3,164,004 A | 1/1965 | King, Jr. |
| 3,393,059 A | 7/1968 | Mosler |

(Continued)

OTHER PUBLICATIONS

Hansen et al, "Multicantilever Biosensors", Methods 37, 2005, pp. 57-64.*

(Continued)

*Primary Examiner* — Joseph W Drodge
(74) *Attorney, Agent, or Firm* — George P Kobler

(57) ABSTRACT

A system is disclosed that comprises a detector module adapted to detect the presence of one or more biological analytes in a fluid. The module includes one or more pairs of microcantilever sensors, where each pair is comprised of a reference sensor and a detection sensor. The detection sensor cantilever is coated with a polymerized receptor that has an affinity with a biological analyte in the fluid. A capture manifold is also provided to receive the fluid downstream of the detector module and comprising the same polymerized receptor such that the biological analytes are removed from the fluid as it courses through the manifold.

24 Claims, 14 Drawing Sheets

(51) Int. Cl.
*G01N 33/569* (2006.01)
*G01N 33/573* (2006.01)

(56) References Cited

U.S. PATENT DOCUMENTS

| | | | |
|---|---|---|---|
| 3,667,619 A | | 6/1972 | Lindblom |
| 3,754,868 A | | 8/1973 | Witz et al. |
| 4,212,719 A | | 7/1980 | Osada et al. |
| 4,519,919 A | | 5/1985 | Whyte et al. |
| 4,609,707 A | | 9/1986 | Nowinski et al. |
| 4,661,226 A | | 4/1987 | Mintz et al. |
| 4,716,024 A | | 12/1987 | Pera |
| 5,055,188 A | | 10/1991 | Johnston et al. |
| 5,147,045 A | | 9/1992 | Chi et al. |
| 5,612,300 A | | 3/1997 | von Blucher et al. |
| 5,719,324 A | | 2/1998 | Thundat et al. |
| 5,728,303 A | | 3/1998 | Johnson |
| 6,036,738 A | | 3/2000 | Shanbrom |
| 6,159,749 A | * | 12/2000 | Liu ................ B01L 3/502 250/251 |
| 6,289,717 B1 | | 9/2001 | Thundat et al. |
| 6,523,392 B2 | | 2/2003 | Porter et al. |
| 6,540,966 B1 | | 4/2003 | Santilli |
| 6,589,727 B1 | * | 7/2003 | Klenerman ...... G01N 33/54373 435/30 |
| 6,596,174 B1 | | 7/2003 | Marcus |
| 6,854,317 B2 | | 2/2005 | Porter et al. |
| 6,872,576 B1 | | 3/2005 | McIntyre |
| 6,926,864 B2 | * | 8/2005 | Peeters ................ B01L 3/5025 422/50 |
| 7,168,294 B2 | | 1/2007 | Porter et al. |
| 7,313,945 B2 | | 1/2008 | Giri et al. |
| 7,510,687 B2 | | 3/2009 | Mazzeo et al. |
| 7,694,346 B2 | * | 4/2010 | Adams ................ G01N 29/036 250/234 |
| 7,794,657 B2 | | 9/2010 | Stewart |
| 7,972,615 B2 | | 7/2011 | Orgambide et al. |
| 8,349,258 B2 | * | 1/2013 | Xu .................... G01N 29/036 422/68.1 |
| 8,354,280 B2 | * | 1/2013 | Arenas ................ G01N 29/022 435/286.5 |
| 8,456,150 B2 | * | 6/2013 | Shih .................... G01N 29/075 324/76.11 |
| 8,524,501 B2 | | 9/2013 | Adams |
| 8,557,956 B2 | | 10/2013 | Cheng et al. |
| 8,828,733 B2 | | 9/2014 | Porter et al. |
| 8,898,069 B2 | | 11/2014 | Hood et al. |
| 8,927,259 B2 | | 1/2015 | Shih et al. |
| 8,961,752 B2 | | 2/2015 | Eberle et al. |
| 2003/0209058 A1 | * | 11/2003 | Merrill ................ G01N 29/036 73/53.01 |
| 2005/0064431 A1 | | 3/2005 | Leon et al. |
| 2006/0047283 A1 | * | 3/2006 | Evans, III ............ A61B 5/076 606/102 |
| 2006/0230817 A1 | * | 10/2006 | Schilowitz .......... G01N 29/022 73/53.01 |
| 2006/0260996 A1 | | 11/2006 | Brownstein et al. |
| 2007/0089515 A1 | | 4/2007 | Shih et al. |
| 2007/0095129 A1 | | 5/2007 | Donaldson et al. |
| 2007/0116607 A1 | * | 5/2007 | Wang ................ B01L 3/502715 422/83 |
| 2007/0145966 A1 | * | 6/2007 | Shekhawat .......... G01N 29/036 324/71.1 |
| 2007/0148437 A1 | | 6/2007 | Muller-Schulte |
| 2008/0035180 A1 | * | 2/2008 | Mutharasan ......... G01N 29/022 134/32 |
| 2010/0072759 A1 | | 3/2010 | Andosca et al. |
| 2010/0151465 A1 | * | 6/2010 | Ju ....................... C12Q 1/6816 435/6.12 |
| 2011/0282175 A1 | * | 11/2011 | Geissler ............... A61B 5/0031 600/365 |
| 2012/0170237 A1 | * | 7/2012 | Canegallo ............... H01L 23/48 361/767 |
| 2014/0113828 A1 | * | 4/2014 | Gilbert ................ H01L 39/126 505/100 |
| 2014/0134607 A1 | * | 5/2014 | Lin ..................... G01N 27/327 435/5 |
| 2014/0287154 A1 | | 9/2014 | Kaiser et al. |
| 2016/0320277 A1 | * | 11/2016 | Avci ...................... G01N 1/405 |

OTHER PUBLICATIONS

Lang et al, "Cantilever Array Sensors", Materials Today, Apr. 2005, pp. 30-36.*
Lam et al, Using microcantilever Deflection to Detect HIV-1, Envelope Glycoprotein gp 120, Nanomedicine Journal 2 2006, pp. 222-229.*
Kale et al, Biofunctionalization of Silicon Nitride-Based Piezo-Resistive Microcantilevers, Sadhana 34, Aug. 2009, pp. 591-597.*
Maheshwari et al, A Technology Overview and Applications of Bio-MEMS Journal of ISSS Sep. 3, 2014, pp. 39-59.*
Alvarez et al, "Microcantilever-based platforms as biosensing tools", The Royal Society of Chemistry, Analyst, 2010, 135, pp. 827-836.*
National Science Foundation, "Microcantilever Applications Overview", Published by Southwest Center for Microsystems Education (SCME) NSF ATE Center, Regents of the University of New Mexico, 2012, Revised Feb. 2017.*
Hansen, et al, Microcantilever Biosensors, Methods 37, 2005, pp. 57-64, Elsevier, US.
Lang, et al, Cantilever Array Sensors, Materials Today, Apr. 2005, pp. 30-36, Elsevier, US.
Lam, et al, Using Microcantilever Deflection to Detect HIV-1 Envelope Glycoprotein gp120, Nanomedicine Journal 2 2006, 222-229, Elsevier, US.
Kale, et al, Bio-functionalization of Silicon Nitride-Based Piezo-Resistive Micocantilevers, Sadhana 34, Aug. 2009, pp. 591-597, IN.
Maheshwari, et al, A Technology Overview and Applications of Bio-MEMS, Journal of ISSS 3, Sep. 2014, pp. 39-59, Inst. of Smart Structures and Systems, IN.

* cited by examiner (A-A)

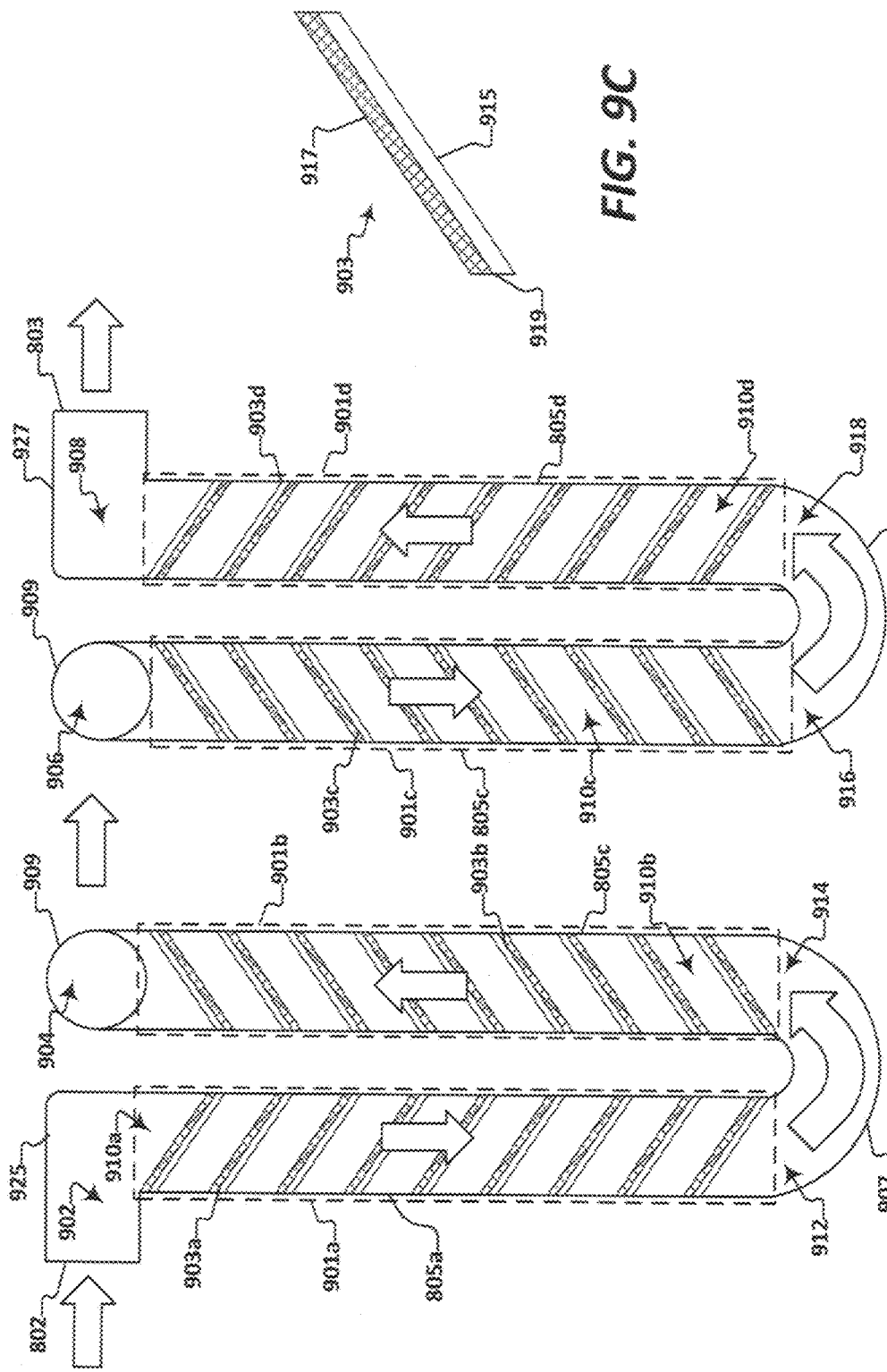

(A-A)

US 10,191,036 B1

SYSTEM FOR DETECTING AND REMOVING BIOLOGICAL ANALYTES IN FLUIDS

BACKGROUND

Technical Field

The present disclosure relates generally to fluids containing biological analytes, and in particular to detection of such biological analytes, and further to detection and removal of biological analytes from fluids.

Description of the Problem and Related Art

Liquid-borne biological contaminants continue to plague mankind in spite of advances in identification of such contaminants and remediation methods. Biological contamination of water for public consumption presents significant health and safety issues. According to the U.S. Environmental Protection Agency (EPA), drinking water may currently contain viruses and bacteria which may cause respiratory illness (Adenovirus), gastrointestinal illness, kidney failure (e.g., *E. coli*), liver disease (Hepatitis A), lung diseases (*Legionella pneumophila*). Current methods of removal include, in addition to mechanical filtering, mixing of antibiotic solutions with the water at water treatment plants. But, this may have harmful effects on the public as well.

Similarly, biologically contaminated fuel is a major concern in the transportation industry. In particular, contaminated fuel has been linked to severe degradation in engine efficiency, and engine malfunction. Fuel biological contaminates include: bacteria, such as *Bacillus, Micrococcus, Pseudomonas*, and *Arthrobacter*; fungi, such as *Hormoconis resinae, Aspergillus*, and *Fusarium*; and yeasts, such as *Penicillum* and *Candida Keroseneae*.

Although, fuel leaves a refinery in a substantially uncontaminated condition, biocontamination occurs in the fuel as a result of the distribution and storage procedures delivery methods, trucks, flowing through pipes, shipped as marine cargo and transferred into bulk storage facilities all provide the means for water and particulates accumulation, harbingers for the production of microbiological contamination. Biocontamination results in engine sludge formation, metal corrosion, decreased lifetime of engine parts, injector fouling, engine flameouts, increased water and Sulphur content in the fuel, oxygen and hydrogen scavenging, sulfate reduction, biosurfactant formation, fuel molecule metabolism and damaging organic coatings on engine parts. Current maintenance procedures on engines that have burned contaminated fuel are to simply remove and replace the affected engine parts. Likewise, hydraulic fluids are subject to deterioration due to biocontamination from spoilage bacteria, yeasts, and fungi.

Typical testing techniques to detect and identify biocontamination in fluids have substantial shortcomings. First, there are some procedures, such as visual observation of the fuel, gravimetric tests, ultraviolet light to look for solid, non-biological contamination, or water. The only way to test for biological contamination is to send a sample of the fluid to an off-site laboratory. One method that has been developed to detect not only microbial contamination, but also non-biological particulates in fluids such as water and air, is disclosed in U.S. Pat. Nos. 8,647.860, "Pathogen and Particle Detector System and Method," to *Jiang, et al.* and 8,427,641, "Compact Detector for Simultaneous Particle Size and Fluorescence Detection," to *Babico, et al.*, both owned by Azbil Biovigilant, Inc., of Tuscon, Ariz. These systems employ ultraviolet light to excite certain metabolytes in biocontaminants. However, while these systems may provide near-real-time indication of detection, they are not designed to be used at the point of use of the fluid, nor are they cost-effective or disposable. Moreover, such systems that rely on light require complex optics that are subject to degradation and failure meaning the optics must be maintained in order for the systems to work.

In the fields of pharmacogenetics, cancer and HIV detection and prediction of heart attacks, biological analytes such as antigens, are tested using the well-known Enzyme Linked Immunosorbent Assay (ELISA) wherein fluid samples containing targeted antigens are placed in a fluid array microtiter plate and antibodies for the targeted antigens that are linked to an enzyme are applied to the antibody array. The enzyme's substrate is next applied causing a reaction that may, in most cases, produce a detectable change in fluid color, thus, identifying the antigens. This method, however, has several shortcomings. ELISA tests are often conducted in a lab environment where the necessary equipment and fluid antibodies are stored. Consequently, the test is not portable. There have been portable test kits developed that may provide detection results on site, but these kits typically require carrying the necessary antibody fluids along with one or more array plates. Further, there must be a separate test run for each antigen.

Thus, there are few techniques or devices that allow on-site, immediate testing with near real-time results for biological analytes in a fluid that are cost effective, and easy to use. Moreover, there are very few, if any, biocontamination remediation methods that do not use mechanical filtering or chemical treatment and none that are deployed at the point of use.

SUMMARY

For purposes of summary, certain aspects, advantages, and novel features are described herein. It is to be understood that not necessarily all such advantages may be achieved in accordance with any one particular embodiment. Thus, the apparatuses or methods claimed may be embodied or carried out in a manner that achieves or optimizes one advantage or group of advantages as taught herein without necessarily achieving other advantages as may be taught or suggested herein.

In one embodiment, the system comprises a detector module adapted to detect the presence of one or more biological analytes in a fluid that includes one or more pairs of microcantilever sensors, where each pair is comprised of a reference sensor and a detection sensor. The detection sensor cantilever is coated with a polymerized receptor that has an affinity with a biological analyte in the fluid. A capture manifold is also provided to receive the fluid downstream of the doctor module and comprising the same polymerized receptor such that the biological analytes are removed from the fluid as it courses through the manifold.

In another embodiment, the detector module comprises one or more arrays of at least one microcantilever sensor pair. Each array is configured to detect a targeted biological analyte with each detection sensor in an array having a corresponding polymerized receptor for detecting the presence of the biological analyte.

In yet another embodiment, the detector module is housed on the interior of an inline fluid coupler for detecting the presence of biological analytes in dynamic fluids. In still another, the detector module is housed in a handheld probe for detecting the presence of biological analytes in static fluid samples. In each case, the detector module may be disposable.

A further embodiment includes a capture manifold with one or more capture stages, one capture stage for each targeted biological analyte where each stage is configured with the polymerized receptor corresponding to the targeted biological analyte. One version of this embodiment, includes a removable cartridge for each stage, and yet another version includes a microbead filter in each stage where the microbeads are formed from a polymerized receptor corresponding to the biological analyte to be removed from the fluid.

One or more embodiments may also include a handheld, computer-based device for receiving biological analyte detection signals from the detector module which is configured with a means for wireless communicators.

These and other embodiments will became readily apparent to those skilled in the relevant arts from the following detailed description having reference to the attached figures.

BRIEF DESCRIPTION OF THE DRAWINGS

The system and method disclosed below are described with reference to the accompanying drawings. In the drawings, like reference numbers indicate identical or functionally similar elements. Additionally, the left-most digit(s) of a reference number identifies the drawing in which the reference number first appears.

FIGS. 9A & 9B show stages of the manifold of FIG. 8 including exemplary contaminant capture elements;

FIG. 9C is a detailed view of one exemplary contaminant capture element as described with reference to FIGS. 9A & 9B;

DETAILED DESCRIPTION

The various embodiments of the system for detecting and removing biological analytes in fluids and their advantages are best understood by referring to FIGS. 1 through 16 of the drawings. The elements of the drawings are not necessarily to scale, emphasis instead being placed upon clearly illustrating the novel features and principles of operation. Throughout the drawings, like numerals are used for like and corresponding parts of the various drawings.

Furthermore, reference in the specification to "an embodiment," "one embodiment," "various embodiments," or any variant thereof means that a particular feature or aspect described in conjunction with the particular embodiment is included in at least one embodiment. Thus, the appearance of the phrases "in one embodiment," "in another embodiment," or variations thereof in various places throughout the specification are not necessarily all referring to its respective embodiment.

Figure 1:
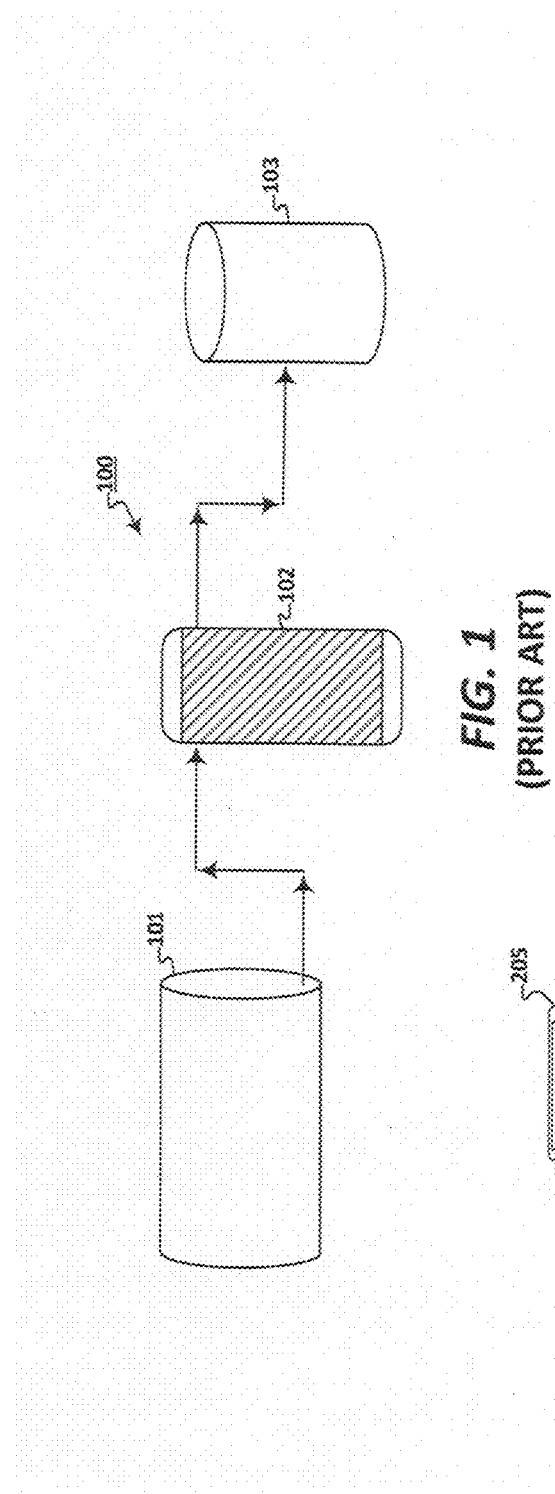
FIG. 1 illustrates a prior art fluid cleaning system.
Figure 2:
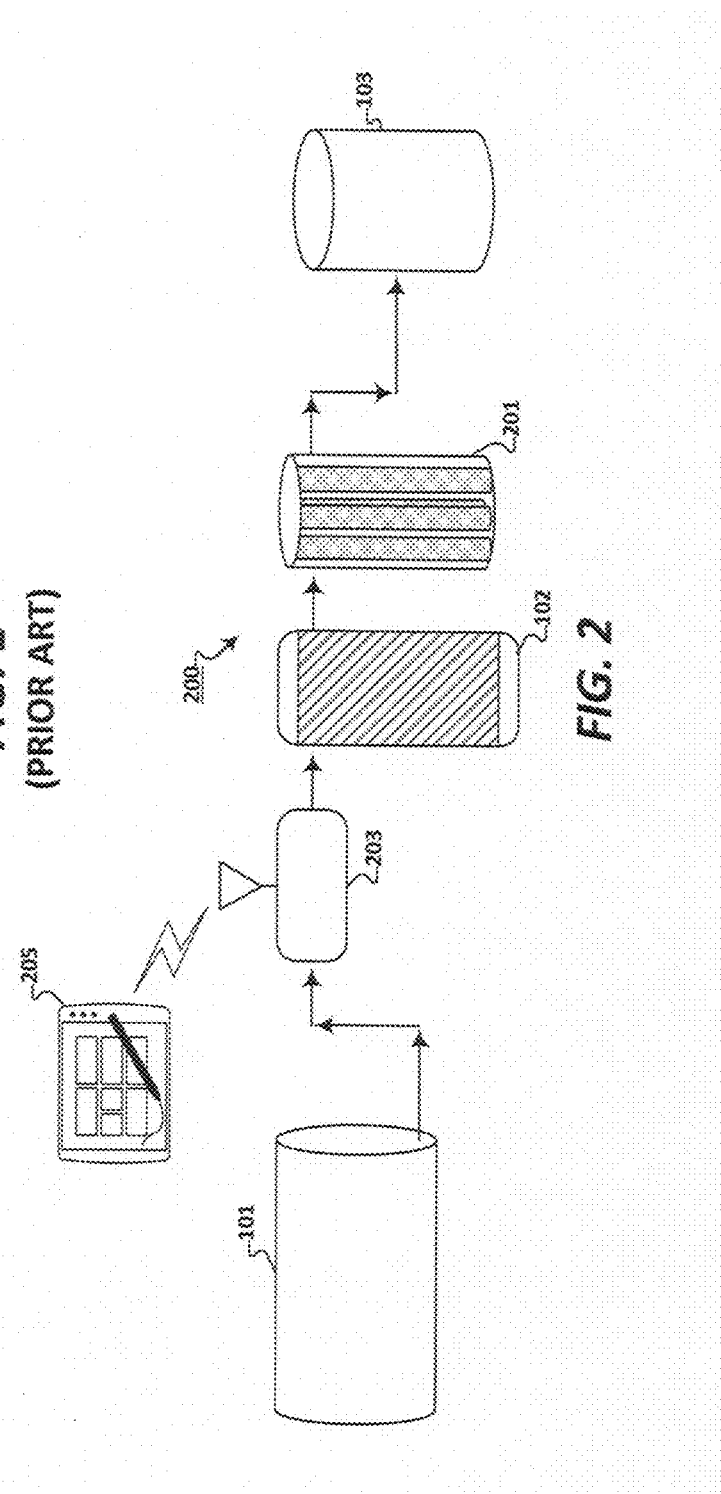
FIG. 2 illustrates an exemplary fluid cleaning with a biological analyte detection coupler and contaminant capture manifold.

FIG. 1 is a simple diagram of the current system 100 and method for a cleaning fluid, which may be water, fuel hydraulic fluid. Fluid may also be a gas which may comprise biological analytes. The fluid is conveyed from a fluid supply 101 through a fluid conduit to filter 102, which removes some water or solid particulates, and then the fluid is ported through a conduit to a fluid reservoir or other receptacle 103 for later use. It can be seen there is no apparatus for removing biological analytes from the fluid. By contrast, FIG. 2 shows one embodiment of the present system 200 wherein a detection coupler 203 is interposed between the storage tank 101 and the filter 102. The coupler 203 comprises a detector module, described in greater detail below, which samples the fluid, and identifies and quantifies the biological analytes therein. Biological analyte data is collected in the module and may be downloaded or transmitted from the sample to interested parties. Next, fluid leaving the filter 102 is ported to a contaminant capture manifold ("CCM") 201, also described in detail below. The CCM removes biological analytes while the fluid is passing through the manifold. The fluid then continues on its way to the fluid reservoir 103. Optionally, a second coupler 203 may be interposed between the manifold 201 and the fluid reservoir 103 to reanalyze the outgoing fluid as it leaves the manifold 201.

Recently, sensors have been developed that employ microelectromechanical systems (MEMS) for detection of biological organism, antigens, and other biological material. For example, many such methods use a MEMS device that includes a microcantilever, examples of which are described in U.S. Pat. No. 5,719,324, "Microcantilever Sensor," to *Thundat, et al.*, U.S. Pat. No. 6,289,717, "Microelectromechanical Antibody Sensor," to *Thundat, et al.*, U.S. Pat. No. 6,523,392, "Microcantilever Sensor," to *Porter et al.*, U.S. Pat, No, 8,927,259, "Piezoelectric Microcantilever Senses for Biosensing," to *Shih, et al.*, and Hansen and Thundat, "*Microcantilever Biosensors,"Methods*, Vol. 37, pp. 57-64 (2005). Typically, the cantilever comprises a coating which includes antibodies, ligands, antigens or other molecular attractors, hereafter referred to as "receptors," which have an affinity to an analyte in a fluid such that the coating absorbs the analyte. Absorption of analytes causes the cantilever to vibrate at a certain resonance frequency that can be measured. In addition, the cantilever will bend in response to molecular absorption and such deflection can be detected, either optically or piezoelectrically. However, to date, such biosensors have not been deployed to provide near-real-time analysis of microbial contamination in water, fuel and other fluids.

Figure 3A:
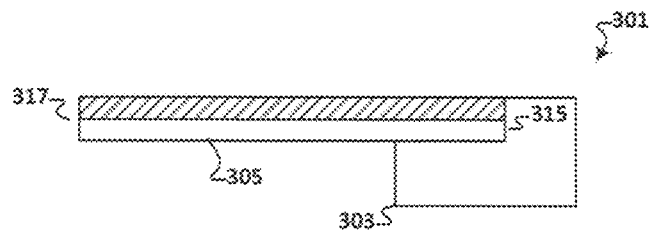
FIGS. 3A through 3D shows the operation of a microcantilever microelectromechanical system (MEMS)
Figure 3B:
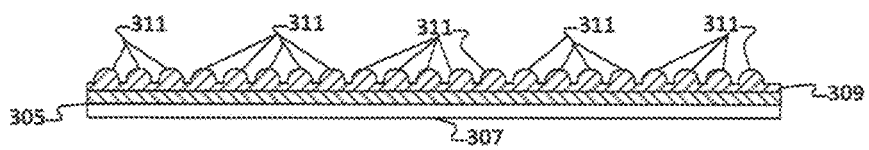
Figure 3C:
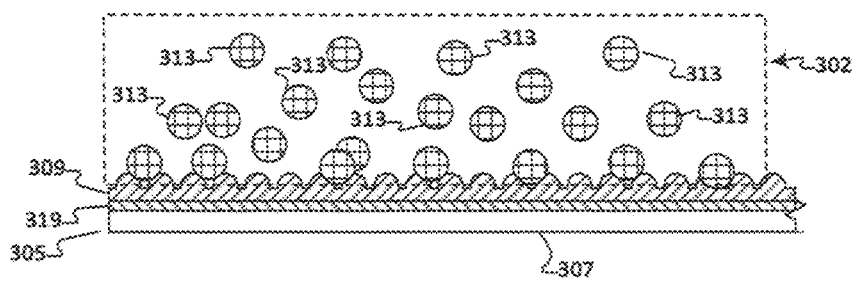
Figure 3D:
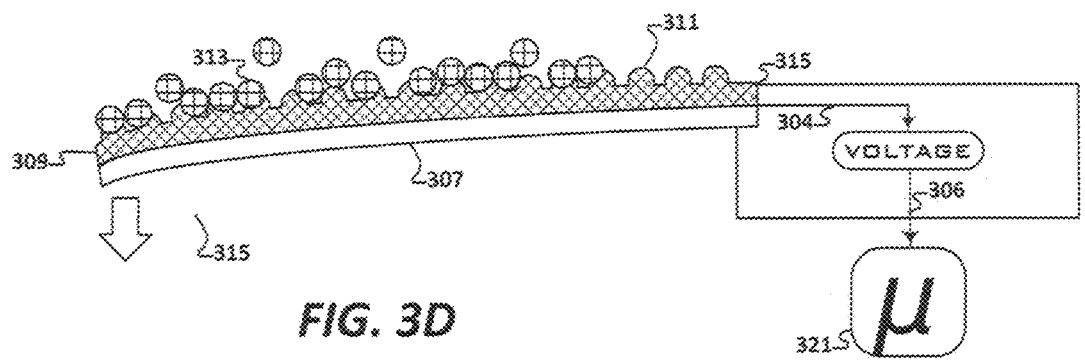

FIG. 3A depicts an example of a microcantilever sensor element 301 contemplated for use in a detection module (FIGS. 4A-4C) deployed in the coupler 203. The microcantilever element 301 is a micro-electromechanical (MEMs) sensor and essentially comprises a cantilever 305 having one end attached to a base 303 which acts as a fulcrum. The opposite end is free from attachment and thus the cantilever is allowed to bend. As shown in FIGS. 3B through 3C, one type of microcantilever element 301 used in the detection coupler 201 uses a cantilever 305 comprising a substrate 307 that is specially coated. The coating comprises at least a receptor layer 309 which is a polymer with integrated receptors 311 for which biological contaminant analytes 313 have affinity. In some embodiments, the polymer coating is a disposable molecularly imprinted polymer (MIP).

In yet other embodiments, it is beneficial to include a "primer" or "sacrificial" layer 319 that bonds the receptor layer 309 with the substrate. The material for this layer may comprise a prepolymer substance, suitable examples of which are para-xylene (PX),1-vinyl-2-pyrrolidinone (VP) polyvinyldifluoride (PVDF) phosphorous glass (SiPOC). Analytes 313, which are to be understood as those targeted biological analytes for which the fluid is being tested, are attracted to the receptors 311 in the receptor layer 309. As the analytes 313 accumulate on the cantilever 305 and are absorbed, a differential surface stress results between the substrate 307 and the receptor layer 309 causing the cantilever 305 to deflect. The degree of deflection may be accurately measured where the cantilever comprises a piezoelectric or piezoresistive material. Thus, upon deflection the cantilever 305 causes an electrical impulse 304 to be generated. The voltage of the impulse 304 is measured and a signal 306 corresponding to the measured voltage is coupled to a microprocessor 321 for further processing. Alternatively, the deflection of the cantilever 305 may be detected using optical or laser measurement.

Figure 4A:
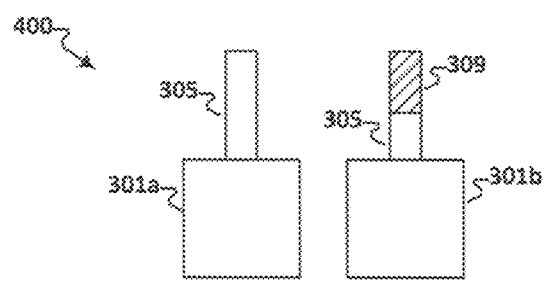
FIG. 4A depicts an exemplary MEMS biological analyte detector array.

The above-described MEMS sensors 301 are deployed in the FEAM which is essentially a biological analyte detector 400, a first exemplary embodiment of which is illustrated in FIG. 4A. The detector 400 comprises at least a pair of MEMS sensors 301 disposed on a circuit board configured as a microprocessor 405, for example, an integrated chip. An "activated" sensor 301b comprises a microcantilever 305 that is coated with a polymer having integrated receptors that are identified as having an affinity for a targeted biological analyte 313. A reference sensor 301a comprises a microcantilever 305 absent such coating. The reference sensor 301a provides a reference signal such that signals from the activated sensor 301b must be of a certain minimum voltage to be considered a valid detection. In other words, for the system to determine whether a signal represents a true positive test for biological analytes, the signal-to-noise ratio between the activated sensor 301b and the reference sensor 301a must meet a pre-determined signal-to-noise ratio threshold. In this way, the likelihood of false positive results is reduced.

Polymers with embedded receptors have been described in the prior art, for example, in U.S. Pat. No. 4,609,707, "Synthesis of Polymers Containing Integral Antibodies," to *Nowinski, et al.*, and U.S. Pat. No. 6,872,576, "Antigens Embedded in Thermoplastic," to *McIntyre*. Typically, receptors are covalently bonded to a suitable monomer, either directly, or with an intermediary compound, known as a "spacer," to form a monomer/receptor conjugate. The monomer is then polymerized through known methods. One such method, is plasma polymerization, and in particular, a low-energy plasma polymerization process, as has been described in the arts, for example, in Deshmukh and Aydill, "Low-Temperature Plasma Enhanced Chemical Vapor Deposition of $SiO_2$," published in *Applied Physics Letters*, Vol. 65 (1998). Other suitable techniques include atmospheric pressure chemical vapor deposition (AP-CVD) and conformal plasma-induced chemical vapor deposition (CPI-CVD), known in the relevant arts. However, it will be understood that the receptor layer may be applied to the microcantilevers in a variety of ways to achieve the objects of the disclosed apparatus, including those deposition techniques that may be hereafter developed.

In a further embodiment, an exemplary detector 400' comprises an array 411 of a plurality of pairs of activated and reference sensors 301a, b enclosed in a housing 401. The housing is configured with one or more intake ports 403 for allowing fluid to enter from one end of the housing and into the interior of the housing and come into contact with the MEMS sensor array 301a, b. One more outlet ports 409 are disposed distally from the intake ports 403.

A portion of the sensors 301 comprise a plurality of activated sensors 301b each having microcantilevers 305 coated with the appropriate receptor-integrated polymer coating(s) which are designed to have an affinity for a biological analyte 313 in the fluid to be tested 302. The remaining portion of the a comprises a plurality of reference sensors 301a each of which having microcantilevers 305 without the coating(s) 309. The increased number of sensor pairs 301a, b provides a greater level of statistical confidence in positive indications by virtue of a greater sensor sample size. The array may further be divided into portions whereby a first portion of the array is comprised of activated sensors 301b configured with coatings 309 having an affinity for a first specific biological analyte 313. Thus, this portion of the array will detect the first analyte 313. A second portion of the array may comprise a plurality of activated sensors 301b designed to target a second biological analyte 313, and so on, in this manner for as many species of analytes 313 desired to be detected.

The detector may further comprise an RF module 407, which is configured to operate using IEEE 802.11 or 802.15 standard communication protocols, or the like, which may be hereafter developed. In a preferred embodiment, a mounting 413 is provided for mounting the detector 400, 400' to the interior surface of the coupler 203. In this embodiment, the housing 401 along with sensor array 411 is removable from the coupler and may be disposed of and replaced with a clean sensor array 411.

Figure 5:
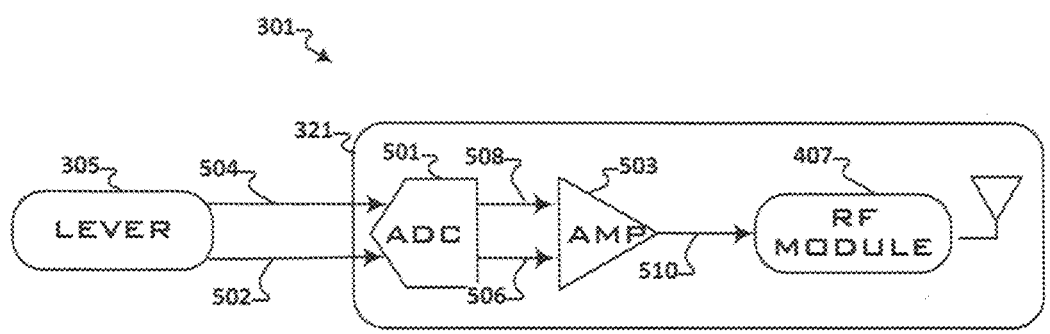
FIG. 5 is a functional schematic of a MEMS microcantilever sensor with a radio frequency module.
Figures 4B, 4C:
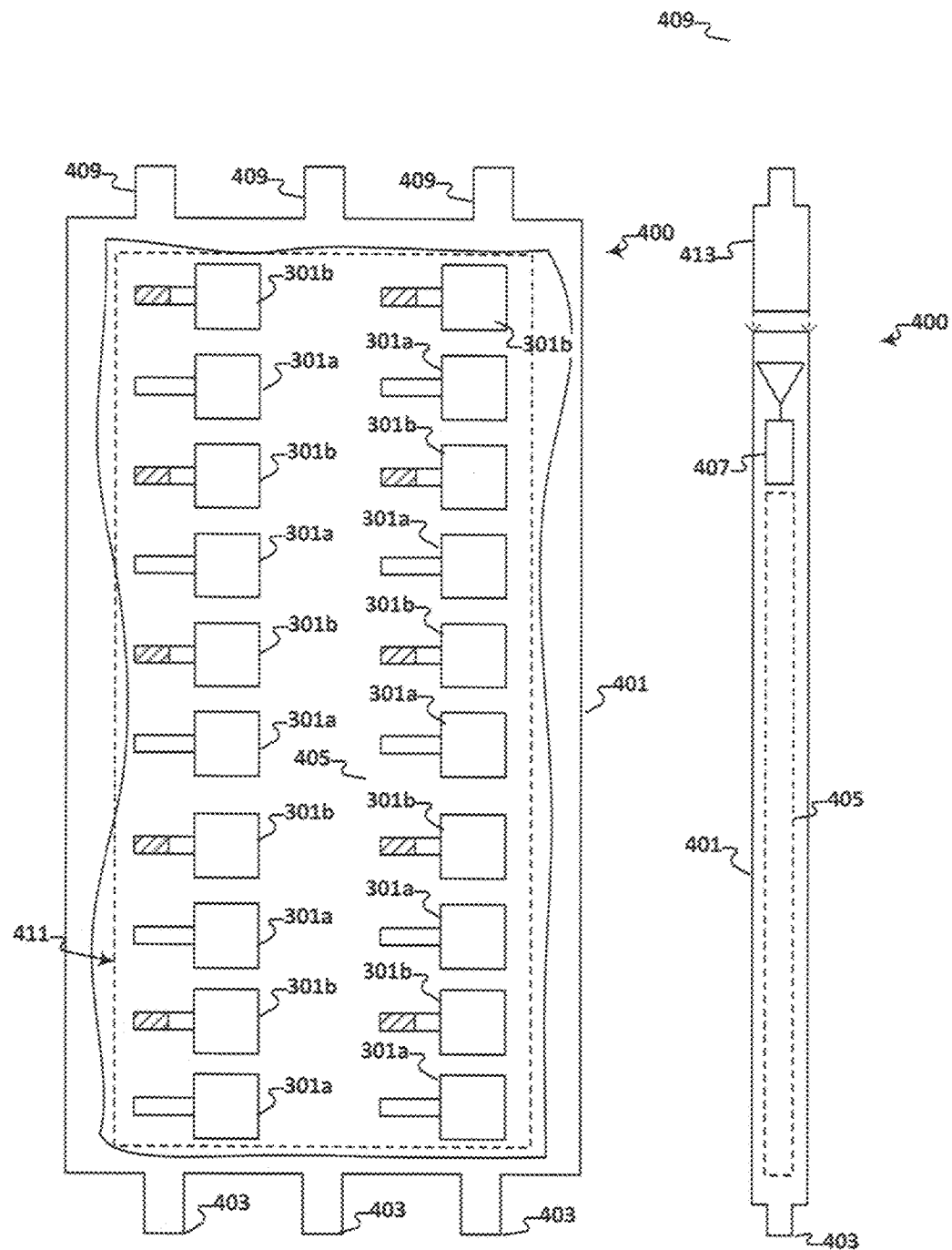
FIG. 4B is a cutaway drawing of a further embodiment of an exemplary biological analyte detector.
FIG. 4C is a side view of the detector shown in FIG. 4B.

FIG. 5 is a functional schematic of a sensor 301 showing the signal path from the microcantilever 305 to the microprocessor 321. The microcantilever 305 generates a voltage in response to piezoelectric effect due to the bending of the cantilever 305. From the reference sensor 301a, the voltage is an analog reference signal 504 retrieved from the reference microcantilevers 305. The detection sensors 301b generates an analog detection signal 502. The analog signals 502, 504 are converted to digital signals 506, 508 respectively, via an analog-to-digital converter 501. The digital signals 506, 508 is amplified by an amplifier 503 which preferably also comprises a comparator that compares the digital detection signal 506 to the digital reference signal 508 to determine whether the voltage difference between the two signals meets the pre-determined threshold. The resulting comparison signal 510 is then coupled to the RF module for transmission.

The microprocessor can be one or more separate processors. Such processors can be implemented by an integrated circuit, a field programmable gated array (FPGA), application specific integrated circuit, fabricated with CMOS, MOSFET, or the similar methods, or a central processing unit (CPU) with a memory or other logic device.

The processor in effect comprises a computer system. Such a computer system includes, for example, one or more processors that are connected to a communication bus. The computer system can also include a main memory, preferably a random access memory (RAM), and can also include a secondary memory. The secondary memory can include, for example, a hard disk drive or a removable storage drive. The removable storage drive reads from or writes to a removable storage unit in a well-known manner. The removable storage unit, represents a floppy disk, magnetic tape, optical disk, and the like, which is read by and written to by the removable storage drive. The removable storage unit includes a computer usable storage medium having stored therein computer software or data. The secondary memory can include other similar means for allowing computer programs or other instructions to be loaded into the computer system. Such means can include, for example, a removable storage unit and an interface. Examples of such can include a program cartridge and cartridge interface (such as that found in video game devices), a removable memory chip (such as an EPROM, or PROM) and associated socket, and other removable storage units and interfaces which allow software and data to be transferred from the removable storage unit to the computer system. Computer programs (also called computer control logic) are stored in the main memory or secondary memory.

Computer programs can also be received via the communications interface. Such computer programs, when executed, enable the computer system to perform certain features of the present invention as discussed herein. In particular, the computer programs, when executed, enable a control processor to perform or cause the performance of features of the present invention. Accordingly, such computer programs represent controllers of the computer system of a transceiver. In an embodiment where the invention is implemented using software, the software can be stored in a computer program product and loaded into the computer system using the removable storage drive, the memory chips or the communications interface. The control logic (software), when executed by a control processor, causes the control processor to perform certain functions of the invention as described herein. In another embodiment, features of the invention are implemented primarily in hardware using, for example, hardware components such as application specific integrated circuits (ASICs) or FPGAs. Implementation of the hardware state machine so as to perform the functions described herein will be apparent to persons skilled in the relevant art(s). In yet another embodiment, features of the invention can be implemented using a combination of both hardware and software.

Advantageously, piezoelectric MEMS devices have been also used as energy harvesters. The MEMS energy harvester consists of a cantilever with a piezoelectric layer (aluminum nitride) sandwiched between metallic electrodes to form a capacitor. A mass attached to one end of the cantilever, enables it to act as a transducer converting vibrations into electricity as the piezoelectric layer flexes. The voltage across the capacitor can then be harvested to drive wireless circuits. Each MEMS is able to generate up to about 250 $\mu W/cm^3$. Thus, the sensor array may generate its own power needs, supplying power for the microprocessor 405 and the RF module 407.

Figure 6A:
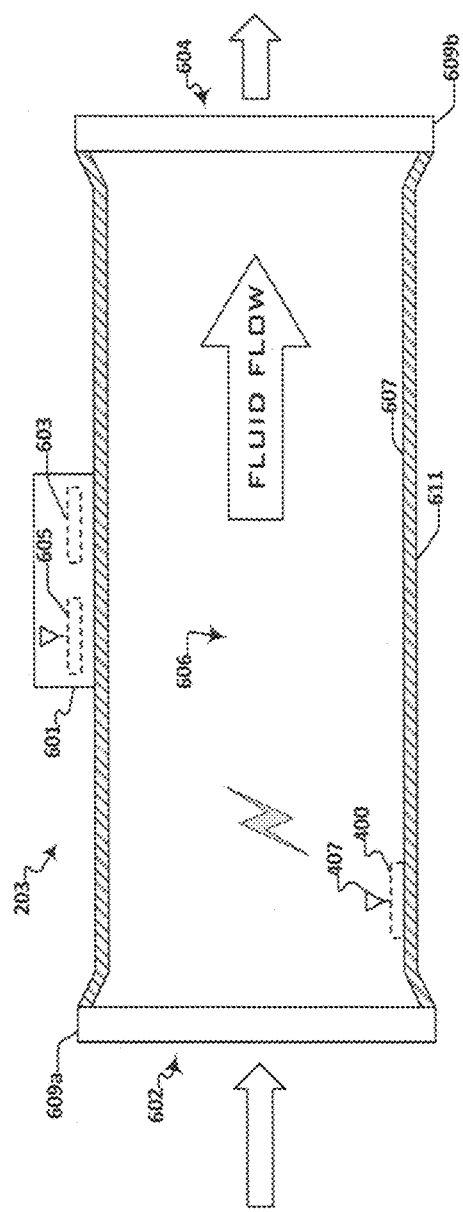
FIGS. 6A & 6B present an exemplary detection coupler incorporating a biological analyte detector.
Figure 6B:
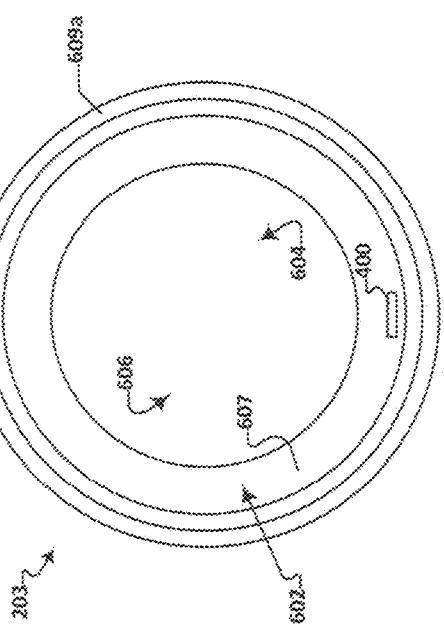

An exemplary embodiment of a detection coupler 203 is shown in FIGS. 6A & 6B and comprises a generally cylindrical body 611 defining a hollow cylindrical chamber 606 having an inlet opening 602 and an outlet opening 604 which are defined by inlet and outlet couplings 609a, b. The couplings 609a, b, the inlet and outlet openings 602, 604, as well as the hollow chamber 606 are dimensioned according to fluid flow rate requirements. The detector 400 is attached to an interior surface 607 of cylindrical body 611 wall. The detection coupler 203 further comprises an adjunct outer housing 601 which encloses a second RF module 605 and a power supply 603 for powering the RF module 605. In operation, results from the detector 400 are transmitted to the RF module 605 which relays the resulting data to a remote device (FIG. 2) which may be any computer-based handheld device 205 with a communications capability. Such a device 205 may be any computer-based device, such as a computer-based tablet, smartphone, or other computer device configured to receive such signal, to store the data in a computer-readable medium for later download, transmission or retrieval, and to display and results to a user. The RF module 605 is configured to operate according to IEEE 802.11 or 802.15 communication protocols, or similar protocols.

Figure 7:
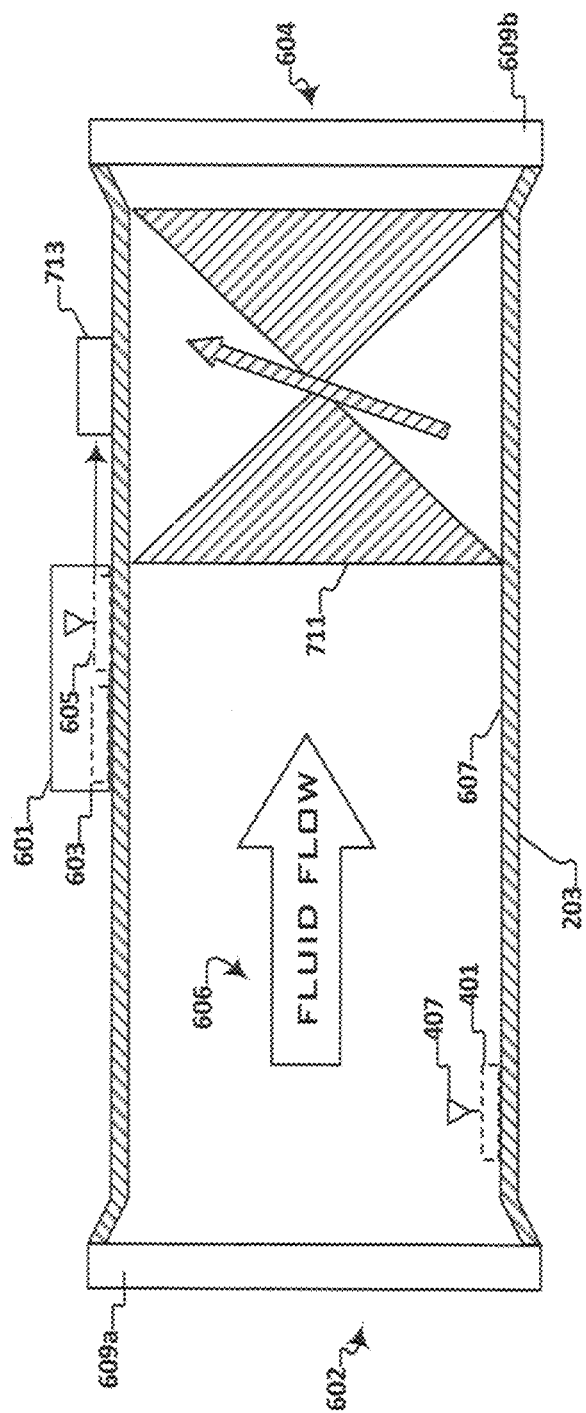
FIG. 7 is a section view of a second embodiment of a detection coupler.

In FIG. 7, another embodiment of the detector coupler 203 is illustrated in which the coupler 203 further comprises a cut-off valve 711 within the hollow chamber 606 disposed toward the outlet end thereof. The cut-off valve 711 is responsive to an actuator 713 which is itself responsive to signals from the RF module 605. In this configuration, when the detector 400 detects the presence of biological analytes, and transmits the data to the RF module 605, the RF module relays a signal to the actuator 713 to close the cut-off valve 711.

Figure 8:
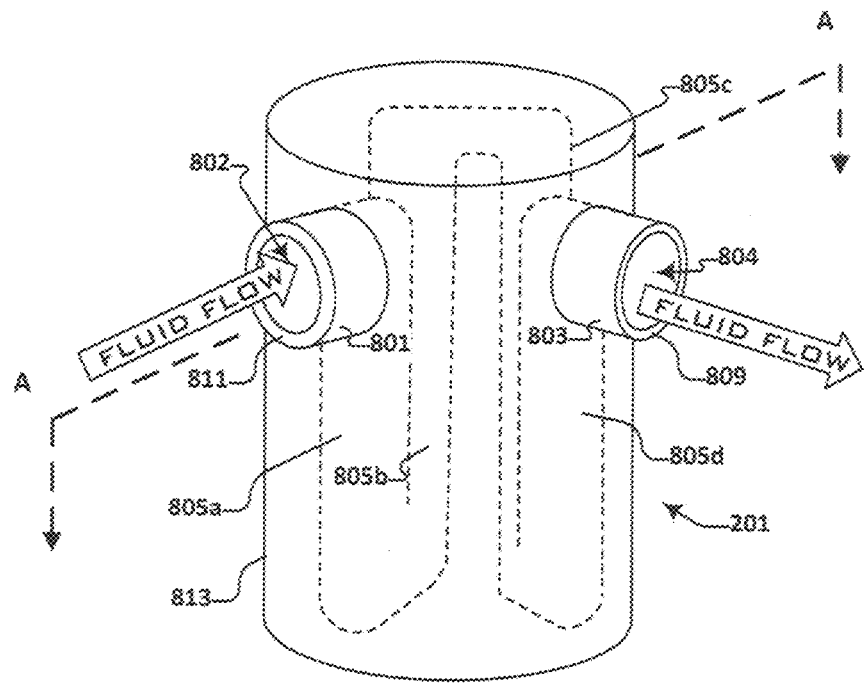
FIG. 8 is an illustration of an exemplary contaminant capture manifold for use in the system of FIG. 2.
Figure 8A:
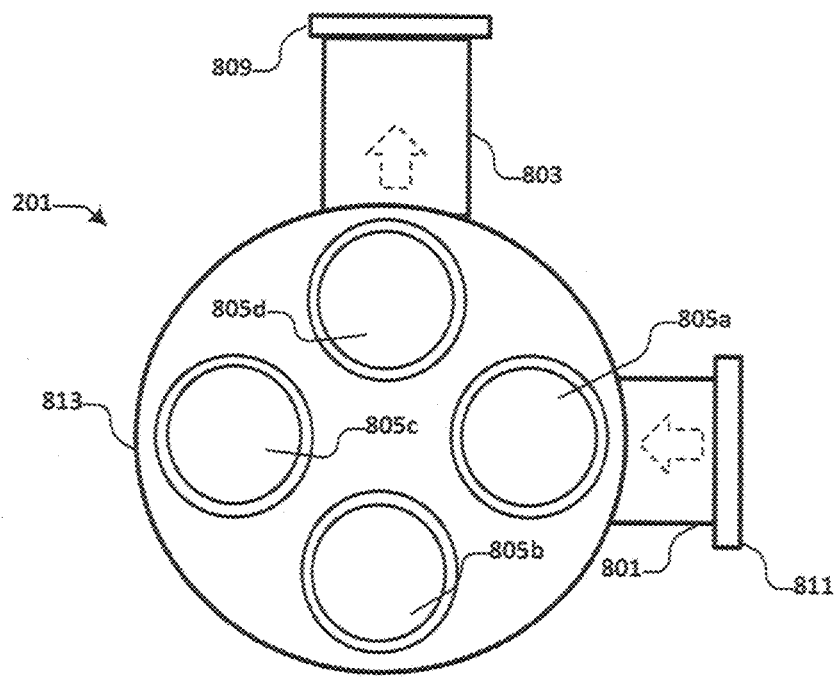
FIG. 8A is a section view of the contaminant capture manifold of FIG. 8 along line A-A.

Referring now to FIGS. 8 & 8A, an example of a contaminant capture manifold (CCM) 201 is presented. The CCM 201 comprises a housing 813 having a fluid inlet 801 with a coupling 811 that is dimensioned to couple to an incoming fluid line (not shown). The coupling 811 defines an inlet opening 802 through which fluid entering the manifold 201 flows. Likewise, an outlet 803 is disposed on another side of the housing 811 with an outlet coupling 809 that is dimensioned to couple to an outflow fluid line (not shown) and that defines an outlet opening 804 through which fluid exiting the manifold flows. Optionally, a second detector 400 may be placed in the CCM outlet 804 to confirm removal of the desired biological analytes. The CCM 201 comprises a plurality of conduits 805a-d, referred to herein as "stages," illustrated in greater detail in FIGS. 9A & 9B.

The first stage 805a includes a first stage inlet having an inlet 902 defined by elbow 925 and in communication with a the CCM inlet opening 802. The first stage inlet 902 is then in communication with a hollow chamber 910a which is defined by the first stage 805a. The chamber 910a terminates in a first stage outlet 912 in communication with an elbow conduit 907 which then leads to a second stage inlet 914. This inlet 914 opens to another hollow chamber 910b which terminates in the second stage outlet 904. Second stage outlet 904 is in fluid communication with an elbow conduit 909 which in turn is in fluid communication with the inlet to the third stage 906 that opens to a third hollow chamber 910c. As with the first two chambers 910a, b, this chamber 910c terminates in a third stage outlet 916 that opens to a second elbow conduit 911. A fourth stage inlet 918 extends from the distal end of the elbow conduit 911 which opens to the fourth stage chamber 910d. This chamber 910d allows fluid to flow into the fourth stage outlet 908 which is defined by elbow 927 and which opens to the CCM outlet 803. Fluid flows through the CCM inlet 802 to the first stage inlet 902 and into the first chamber 910a, to the first stage outlet 912 and into the first elbow conduit 907 flowing then into the inlet to the second stage 914. The fluid then passes through the second stage chamber 910b to the second stage outlet 904 and through the second elbow conduit 909 before it enters the third stage 805c through the third stage inlet 906. The fluid will travel through the third stage chamber 910c to the third stage outlet 916 and through the third elbow 911 after which it will flow through the inlet 918 to the fourth stage, through the fourth stage chamber 910d and the fourth stage outlet 908 and finally exit through the CCM outlet 803.

Each stage 805a-d comprises a contaminant capture section 901a-d which comprises a contaminant capture element 903a-d for capturing biological analytes in the fluid. In this embodiment, the contaminant capture element 903 comprises a spiral ramp 919, shown in detail in FIG. 9C. The ramp 919 includes a substrate and a polymerized receptor coating 917 which is infused with a receptor having an affinity with a biological analyte 313 in the fluid. The polymerized coating 917 is preferably the same coating used for the sensors 301a in the detector 400. Accordingly, as the fluid passes through a stage 805, biological analyte 313 in the fluid will be drawn to the corresponding receptors 311 in the coatings 917 and retained on the coatings 917 thereby being removed from the fluid. Those skilled in the relevant arts will recognize that to increase the likelihood of capturing the greatest percentage of biological analytes, surface area of the polymerized receptor coatings should be as great as possible. For this reason, the turns of the spiral ramps 903a-d may be increased in each stage 805.

It is envisioned that where a fluid may contain multiple species of biological analyte 313, each contaminant capture section 901a-d will be configured to capture each species of biological analyte 313. In other words, the contaminant capture element 903a of the first capture section 901a may include a polymerized receptor coating 917 designed to capture bacteria, which another section 901b might be configured with coating designed to capture a fungus and so on. It will therefore be understood that while four stages are shown in the above example, the manifold may be adapted to include as many stages 805 as there are targeted biological analyte 313 to be removed from a fluid. Indeed, the manifold may possibly include a single stage 805, or a plurality of stages 805, all of which comprise the same receptor coating 917. Furthermore, a single CCM 201 may comprise a plurality of stages 805 dedicated to capturing one species of contaminant 313 and a second plurality dedicated to capturing a second species, and so on, thus, having a plurality of stages, each plurality dedicated to capturing a species of contaminant 313.

Figure 10A:
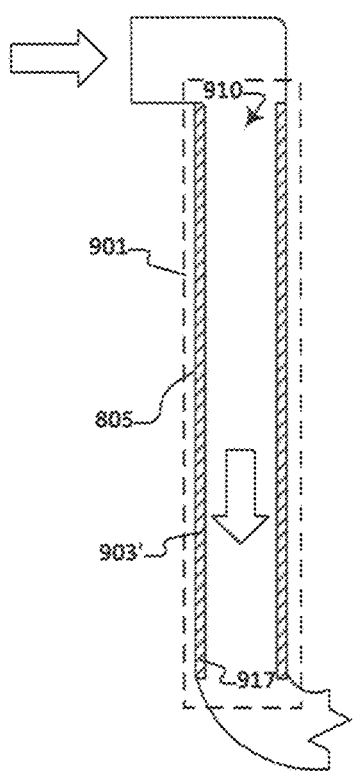
FIGS. 10A & 10B are two views of a manifold stage incorporating another embodiment of a contaminant capture element.
Figure 10B:
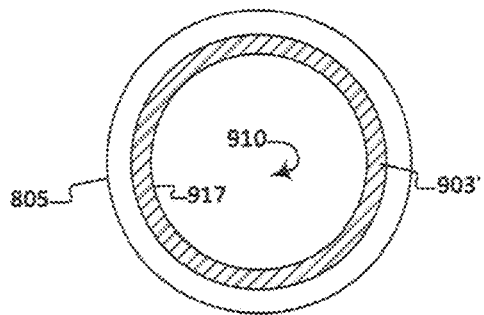
Figure 12D:
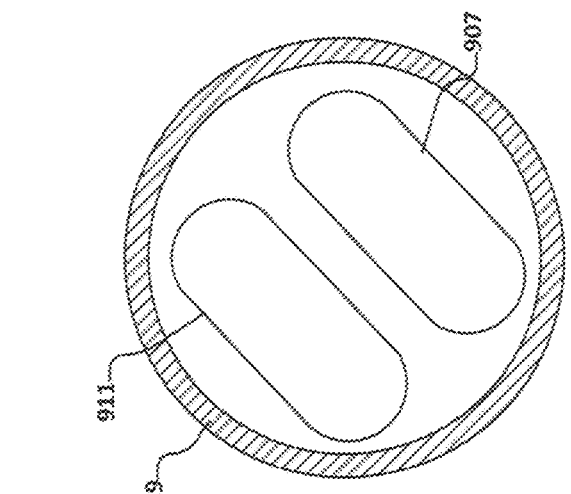
FIGS. 12A through 12D provide illustrations of a further exemplary embodiment of a contaminant capture manifold for use with the contaminant capture section of FIG. 11.
Figure 12C:
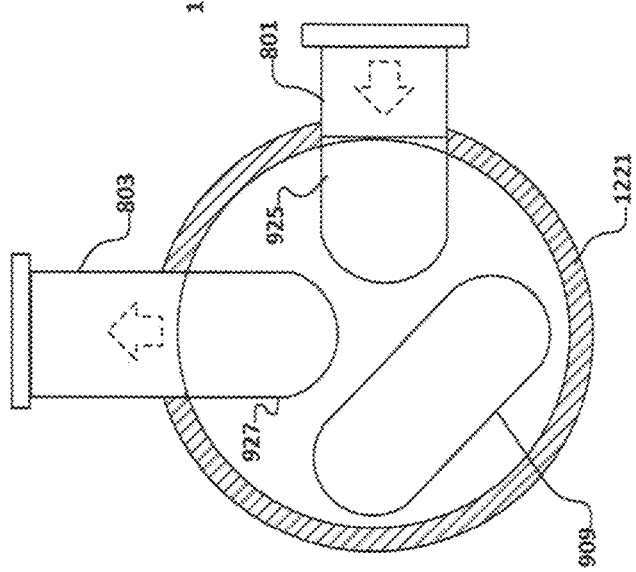
Figure 11:
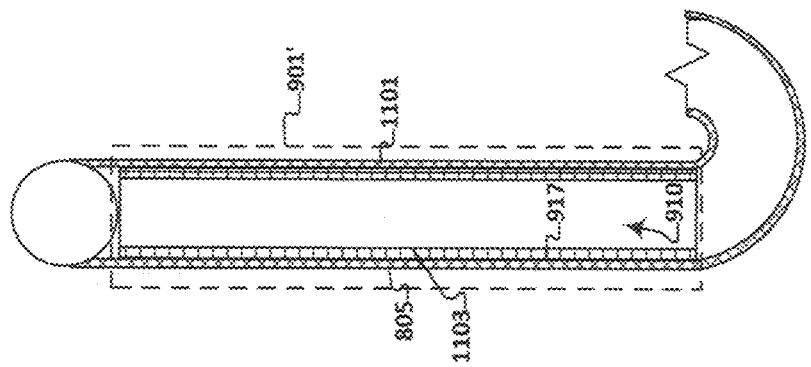
FIG. 11 illustrates a further embodiment of an exemplary contaminant capture section.
Figure 12A:
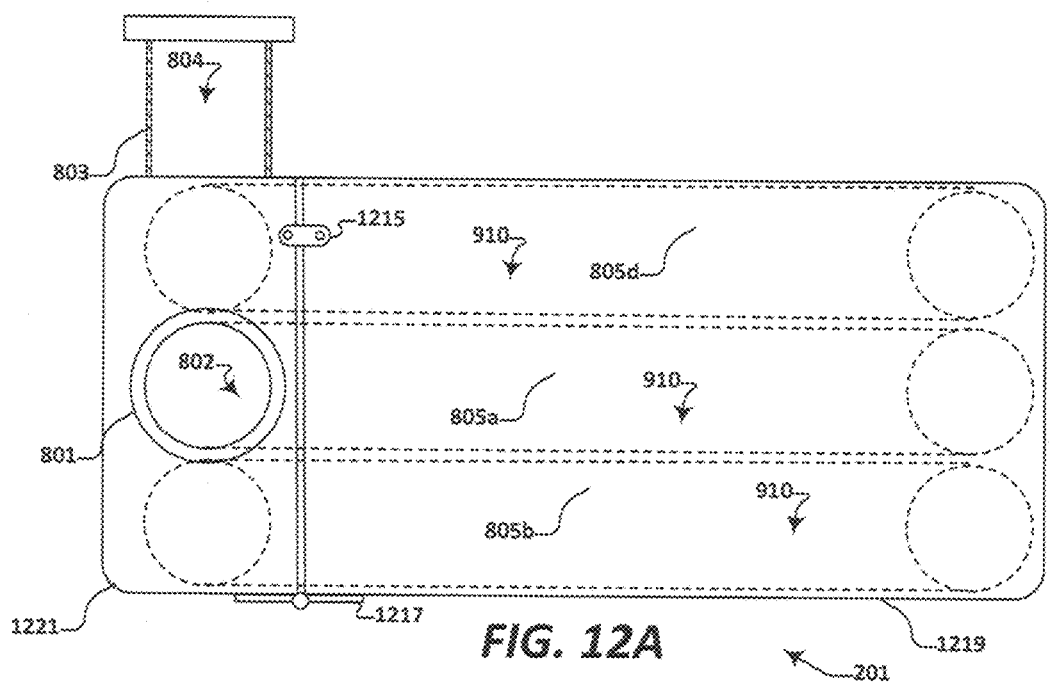
Figure 12B:
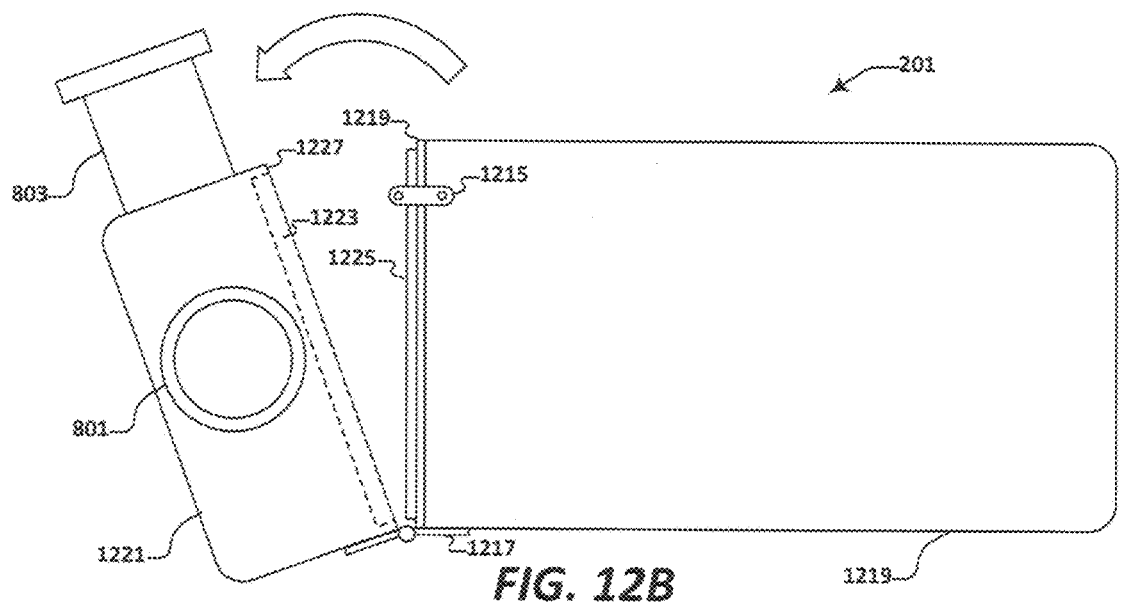

FIGS. 10A & B present a second version of a contaminant capture element 903' which is the polymerized receptor coating 917 applied to the inner surface of the hollow chamber 910 of the stage 805. In yet a further embodiment, the contaminant capture section 901' (FIG. 11) of each stage 805 comprises a contaminant capture element 1103 which is a removable cartridge 1101 that can be slidably inserted into the hollow chamber 910. The cartridge 1101 includes the polymerized receptor coating 917 in any of the embodiments described herein. It will be appreciated the polymerized receptor coating 917 will eventually absorb so much biocontamination that its effectiveness is degraded. Instead of disposing of the entire CCM 201, the cartridges 1101 may be removed and disposed of and replacement cartridges 1101 may be inserted into the chambers 910.

A CCM 201 for use with disposable contaminant capture elements is depicted in FIGS. 12A-12D 1103 comprises a lower housing 1219 to which a lid 1221 is attached with a hinge element 1217. A latch 1215 is provided for retaining the lid 1221 in a closed position vis-à-vis the housing 1219. The lower housing 1219 is configured with an annular shoulder on which sits a gasket 1219. An annular rim 1225 extends from the shoulder. The lid 1221 is configured with an annular recess 1223 defined with its rim 1227 dimensioned to receive the lower housing rim 1225. Thus, when the lid 1221 is closed on the lower housing 1219, the lower housing rim 1225 is inserted into the recess 1223 of the lid and the lid rim 1227 is seated upon the gasket 1219, and the latch 1215 secures the lid 1221 in the closed position. The lid 1221 comprises a generally cylindrical body having the inlet 801 and the outlet 803 and is configured with the "upper" elbows 925, 909 and 927 as described above. Similarly, the lower housing 1219 comprises the hollow chambers 910 for each stage 805 as well as the "lower" elbows, 907 and 911.

Figures 13A, 13B:
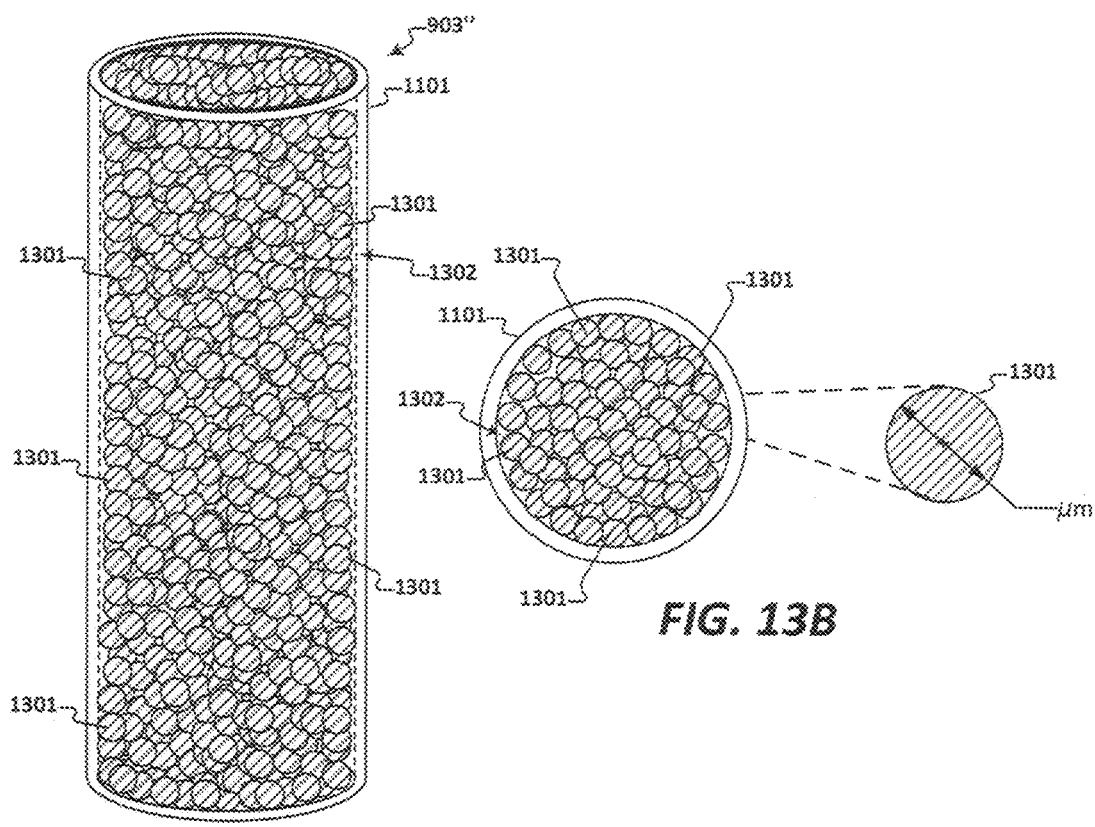
FIGS. 13A & 13B are showing another embodiment of a contaminant capture element.

Yet another version of a contaminant capture element 903" is shown in FIGS. 13A & B comprising a cartridge 1101 having a hollow interior chamber 1302 filled with micro beads 1301 which are formed from the same receptor-infused polymer described above. This element has the advantage of exposing the fluid to be cleaned to a great amount of surface area of the receptor polymer to increase the likelihood of capturing all targeted biological analytes in the fluid.

Figure 14:
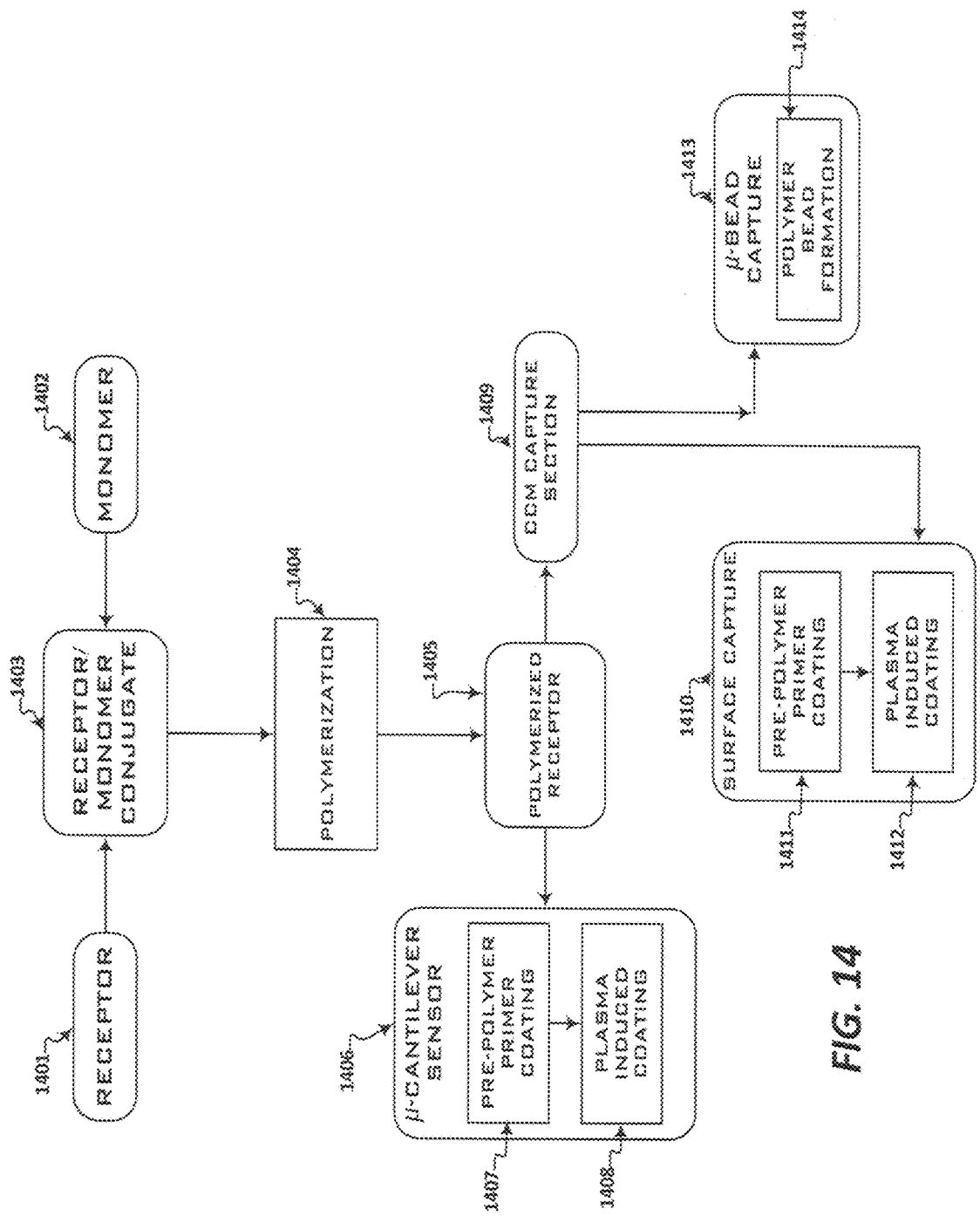
FIG. 14 is a flowchart of an exemplar process for plasma polymerization of receptors for use in the system set forth herein.

An exemplary process for application of the receptor-integrated polymer to the microcantilevers is illustrated in FIG. 14. A receptor is selected based on the degree to which a target biological analyte is attracted to the receptor and will attached to it (Step 1401) while a monomer is chosen 1402. It will be understood that while a monomer has been described, a prepolymer or copolymer may be used as well. Also, care should be taken to select the monomer, etc., with an eye toward the resulting polymer's resistance to degradation as a result of exposure to the fluid environment. For example, it is well known that certain polymers, e.g., polystyrene severely degrades when exposed to hydrocarbon-based fluids such as fuel. At step 1403, the monomer and receptor are bonded to form a receptor monomer conjugate which is then polymerized 1404, forming a polymerized receptor 1405. When applying the polymerized receptor to the microcantilevers 1406, a prepolymer coating is applied 1407 as a primer layer described above then the polymerized receptor is applied using a plasma-induced coating technique 1408 although other suitable deposition techniques may be used. For the capture elements of the contaminant capture manifold 1409, if the contaminant capture element is a surface on a substrate 1410, the polymerized receptor is applied in Steps 1411 and 1412 in the same manner as with the microcantilevers. On the other hand, if the contaminant capture element uses a microbead capture, the polymerized receptor is formed into microbeads at Step 1413.

Table 1 below presents a list of some of the possible biological contaminants that typically contaminate fuel along with the corresponding receptors that may be used to detect and remove such microbial contaminants from the fluid.

TABLE 1

Biocontaminants in fuel and their corresponding receptors.

| Organism | Genus | Receptor |
|---|---|---|
| Acetobacter | Bacteria | Anti-apaLIM Antibody (aa1-429, HRP): LS-C371276, LS-C371278 & LS-C371280 |
| Bacillus | Bacteria | Anti-bacillus ab20556 |
| Micrococcus | Bacteria | Anti-MCAb antibody |
| Pseudomonas | Bacteria | Anti-Pseudomonas antibody (ab68538) |
| Arthrobacter | Bacteria | XPD-L1/B7-H1/CD274, PD-L2/B7-DC/CD273, SHP2/PTPN11 Protein & CD8/CD8 alpha/Leu-2 Protein; polyclonal antibody, DPATB-H82389; Arthrobacter globiformis, Choline oxidase polyclonal antibody |
| Hormoconis resinae | Fungi | H. resinae antiserum antibodies |
| Aspergillus | Fungi | Anti-Aspergillus antibodies: ab20419, ab34953 & ab155839 |
| Fusarium | Fungi | Anti-Fusarium [FvCA4] antibodies: ab01005-1.6 & ab01005-23.0 |
| Penicillum | Fungi | Penicillum antibody: abIN111037 |
| Candida keroseneae | Yeast | Candida Albicans antibody: ab53891, ab21164 |

Table 2 lists some of the possible microbial contaminants found in water, taken from the drinking water contaminant list (CCL 4) promulgated by the U.S. Environmental Protection Agency, along with their corresponding receptors that may be employed in the detection and removal system.

TABLE 2

Microbial contaminants in water and their corresponding receptors.

| Organism | Genus | Receptor |
|---|---|---|
| Campylobacter jejuni | Bacteria | Anti Campylobacter jejuni antibodies: ab54125. ab53909 & ab8063 |
| E. coli | Bacteria | Anti-E. Coli antibodies: CD62E (BBIG-E4). CD62F (BBIG-E1), CD62E |
| Heliobacter pylori | Bacteria | Anti-H. pylori antibodies: Poly29135 Purified anti-H. pylori antibody |
| Legionella pneumophila | Bacteria | Anti Legionella pneumophilia antibodies: ab20819, ab20943, ab69239, ab20561 |
| Mycobacterium avium | Bacteria | Anti Mycobacterium avium antibodies: Antibody (15D10) |
| Salmonella enterica | Bacteria | Anti Salmonella enterica antibodies: [1E6] ab8274 |
| Shigella sonnei | Bacteria | Anti Shigella sonnei antibodies: ab19988 |
| Adenovirus | Virus | Anti-Adenovirus antibodies: ab6982 [8ac4], ab8249 [M73], ab33183, ab223689 & [1E11] |
| Caliciviruses | Virus | Calicivirus antibodies: [FCV-43] ab33990 |
| Enterovirus | Virus | Anit-Enterovirus antibodies: 2Q1929 & 649 |
| Hepatitis A | Virus | Anti-Hepatitis A antibodies: PIP008, MK01 (4939-7029) |

Figure 15:
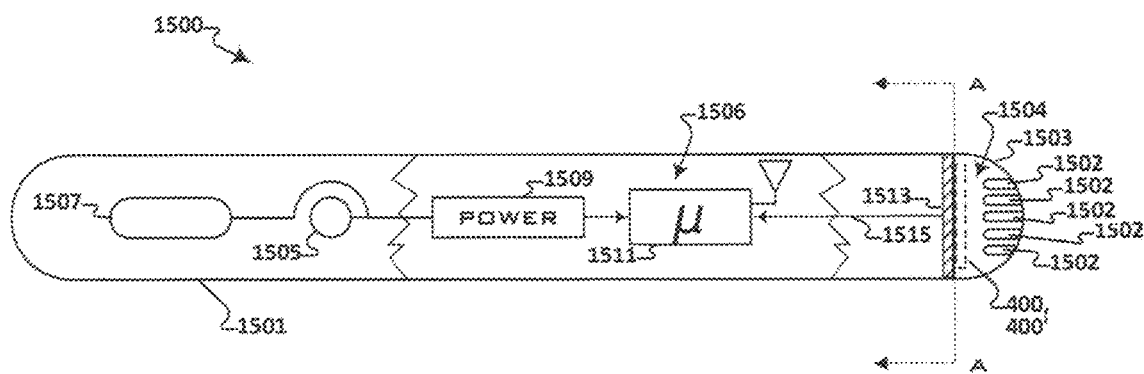
FIG. 15 is a partial cut-away view of a handheld probe comprising the biological analyte detection module of FIGS. 4A through 4C.
Figure 15A:
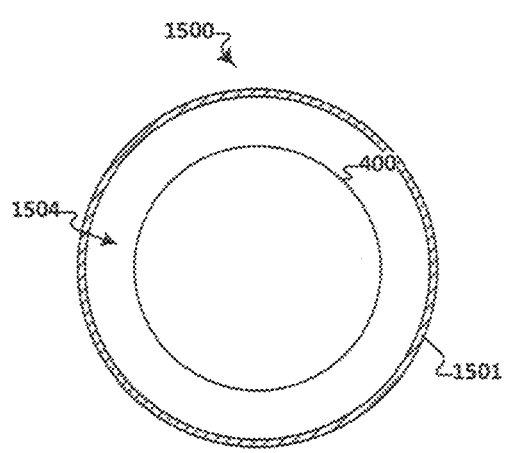
FIG. 15A is a section view along line A-A of the handheld probe of FIG. 15.
Figure 16:
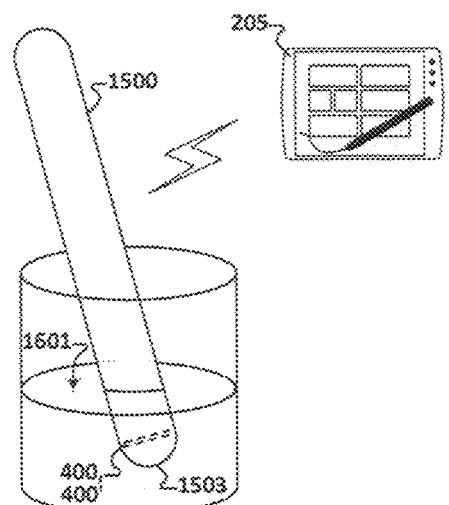
FIG. 16 depicts the use of the handheld probe of FIG. 15.

In addition to the fluid coupler described above, the detector module 400, 400' may also be deployed in an embodiment shown in FIGS. 15, 15A & 16. In this version, the detector module 400, 400' is housed in a handheld probe 1500 comprising a housing 1501 which defines an interior hollow chamber 1506. A microprocessor 1511 and a power supply 1509 are disposed within the chamber 1506. The housing 1501 is further comprised of a switch 1507 connected to the power supply 1509 for selectively energizing the microprocessor 1511 as well as a power on indicator light 1505.

One end of the probe 1500 comprises a second chamber 1504 disposed at one end 1503 of the housing and is defined therein with a wall 1513 separating it from the first chamber 1506. The detector module 400, 400' is disposed within the second chamber 1504 on the surface of the wall 1513 and one or more openings 1502 are defined within the end 1503 of the housing 1501, the openings 1502 dimensioned to allow fluid to enter the second chamber 1504 and come into contact with the detector module 400, 400'. As illustrated in FIG. 16, the operative end 1503 of the probe 1500 may be inserted into a fluid sample 1601 such that the fluid 1601 enters the second chamber 1504 through opening(s) 1502 and comes into fluid communication with the detector module 400, 400'. When the detector module 400, 400' detects the presence of biological analytes 313, it issues a detection signal 1515 to the microprocessor 1511 which, in turn, wirelessly relays the detection signal 1515 to a computer-based handheld device 205, such as a computer-based tablet, smartphone, or other computer device configured to receive such signal, to store the data in a computer-readable medium for later download, transmission or retrieval, and to display and results to a user. Then, in cases where the fluid contains microbial contamination, the fluid may be sent to the contaminant capture manifold describe above for contaminant removal. In some embodiments, the handheld probe 1500 may be comprised of disposable elements.

It will be appreciated that the handheld probe 1500 may be used in detection of biological compounds such as enzymes, for a variety of fluids including blood and saliva to detect antigens comprised therein. The following table shows just some types of the biological analytes that may be detected using the handheld probe 1500 configured as described above. It will be apparent to those skilled in the relevant arts with the benefit of this disclosure that the detection module may be used in a variety of applications, including pharmacogenetics, HIV and cancer detection, and heart attach prediction. The following Table 3 presents those applications, listing the biological analyte and the corresponding receptors.

TABLE 3

Blood- and saliva-borne enzymes and proteins and their corresponding receptors

| Biological Analyte | Type | Application | Receptor |
|---|---|---|---|
| CYP2C9 | Enzyme | Pharmacogenetics | Anti-CYP2C9/Cytochrome P450 2C9 Antibodies: LS-B11732, LS-C97486 |
| CYP2C19 | Enzyme | Pharmacogenetics | Anti-CYP2C19 Antibodies (aa324-373); LS-C110653, LS-C167223, LS-C177035, LS-C358462 & LS-C383003 |

TABLE 3-continued

Blood- and saliva-borne enzymes and proteins and their corresponding receptors

| Biological Analyte | Type | Application | Receptor |
|---|---|---|---|
| CYP2D6 | Enzyme | Pharmacogenetics | Anti-CYP2D6 Antibodies: LS-B13571, LS-C40339, LS-C107627, LS-C109528 & LS-C368579 |
| CYP3A4 | Enzyme | Pharmacogenetics | Anti-CYP3A4/Cytochrome P450 3A4 Antibodies: STJ23326, STJ23325, STJ92594 & STJ92593 |
| CYP3A5 | Enzyme | Pharmacogenetics | Anti-CYP3A5 Antibodies: ST J23337 & ST J23337 |
| HIV protein P24 | Protein | HIV Detection | ab9071, ab9072, ab63917 & ab63958 |
| Alpha fetoprotein (AFP) | Protein | Liver Cancer Detection | Anti-alpha 1 Fetoprotein antibody [AFP-01] (ab3980) |
| CA15-3 | Antigen | Breast Cancer Detection | CA 15.3 antibody (10-1143) |
| CA19-9 | Antigen | Gastric/Pancreatic/Stomach Cancer Detection | CA 19.9 antibody (HRP)(61-1060), CA 19.9 protein (30-AC14) |
| CA125 | Antigen | Uterine Cancer Detection | CA125 antibody (70R-21604), CA125 antibody (HRP) (61-C02A) |
| Carcinoembryonic antigen (CEA) | Antigen | Colorectal Cancer Detection | C6G9, monoclonal |
| Human papillomavirus (HPV) | Protein | Head/Neck Cancer Detection | HPV-6124 |
| Myeloperoxidase (MPO) | Enzyme | Heart Attack Prediction | MPO monoclonal antibodies: 8E6, 2C7, 9B12G7, 4D8B12, 9B12D9, 9C11A5, SP72, 2A11, 4A4; MPO polyclonal antibodies. |

Tables 1, 2 and 3 should be understood to merely present just some examples of the types of biological analytes that the detector module 400, 400' are able to detect. Therefore, the tables should not be construed to limit the possible biological analytes detectable by the detector module 400, 400' to just those analytes listed. It will be apparent to those skilled in the relevant arts that any antibody corresponding to a biological analyte may be used to detect such analyte according to the principles described above. In addition to the receptors described herein, it should be noted that suitable receptors for use in the detector module 400, 400' or in the contaminant capture manifold 201 may be any receptor suitable in an enzyme-linked immunosorbent assay (ELISA) test.

As described above and shown in the associated drawings, the present invention comprises a system for detecting and removing biological analytes in fluids. While particular embodiments have been described, it will be understood, however, that any invention appertaining to the apparatuses, systems, and methods described is not limited thereto, since modifications may be made by those skilled in the art, particularly in light of the foregoing teachings. It is, therefore, contemplated by the appended claims to cover any such modifications that incorporate those features or those improvements that embody the spirit and scope of the invention.

What is claimed is:
1. A fluid cleaning system comprising:
a detector module for detecting the presence of one or more biological contaminants in a fluid, said detector module comprising:
a detector module housing having a fluid outlet;
one or more pairs of microcantilever sensors enclosed within said detector module housing, each said pair comprising a reference microcantilever sensor and a detection microcantilever sensor comprising a polymerized receptor, said polymerized receptor having an affinity with a biological contaminant of said one or more biological contaminants, said detection sensor configured to provide a detection signal in the presence of said one or more biological contaminants; and
a contaminant capture manifold enclosed within a contaminant capture housing having an inlet in fluid communication with, and downstream of said detector module outlet and comprising one or more stages, each said stage comprising a contaminant capture element each said contaminant capture element comprising one of a spiral ramp comprising said polymerized receptor, a cylindrical wall coated with said polymerized receptor, and a plurality of microbeads comprised of said polymerized receptor.

2. The fluid cleaning system of claim 1, wherein said detector module further comprises a radio frequency module for communicating said detection signal generated by said detector module.

3. The fluid cleaning system of claim 2, wherein said polymerized receptor has an affinity for at least one of *Hormoconis resinae, Micrococcus, Pseudomonas, Arthrobacter, Aspergillus, Fusarium, Penicillum, Candida keroseneae, Acetobacter, Campylobacter jejuni, E. coli, Heliobacter pylori, Legionella pneumophila, Mycobacterium avium, Salmonella enterica, Shigella sonnei*, Adenovirus, Caliciviruses, *Enterovirus*, and Hepatitis A.

4. The fluid cleaning system of claim 1, wherein said one or more biological contaminants is at least one of *Hormoconis resinae, Micrococcus, Pseudomonas, Arthrobacter, Aspergillus, Fusarium, Penicillum, Candida keroseneae,*

*Acetobacter, Campylobacter jejuni, E. coli, Heliobacter pylori, Legionella pneumophila, Mycobacterium avium, Salmonella enterica, Shigella sonnei*, Adenovirus, Caliciviruses, *Enterovirus*, and Hepatitis A.

5. The fluid cleaning system of claim 1, wherein said fluid is one of fuel, and water.

6. The fluid cleaning system of claim 1, wherein said fluid is fuel, and wherein one or more of said polymerized receptors have an affinity with at least one of *Hormoconis resinae, Micrococcus, Pseudomonas, Arthrobacter, Aspergillus, Fusarium, Penicillum, Candida keroseneae*, and *Acetobacter*.

7. The fluid cleaning system of claim 1, further comprising a computer-based handheld device responsive to said detection signal.

8. The fluid cleaning system of claim 7, wherein said fluid is one of water, and fuel.

9. The fluid cleaning system of claim 8, wherein said polymerized receptor has an affinity for at least one of *Hormoconis resinae, Micrococcus, Pseudomonas, Arthrobacter, Aspergillus, Fusarium, Penicillum, Candida keroseneae, Acetobacter, Campylobacter jejuni, E. coli, Heliobacter pylori, Legionella pneumophila, Mycobacterium avium, Salmonella enterica, Shigella sonnei*, Adenovirus, Caliciviruses, *Enterovirus*, and Hepatitis A.

10. The fluid cleaning system of claim 1, wherein said one or more pairs of microcantilever sensors comprises one or more arrays comprised of a plurality of pairs of microcantilever sensors, each of said arrays comprising a plurality of said detection microcantilever sensors to detect one of said one or more biological contaminants.

11. The fluid cleaning system of claim 10, wherein said polymerized receptor has an affinity for at least one of *Hormoconis resinae, Micrococcus, Pseudomonas, Arthrobacter, Aspergillus, Fusarium, Penicillum, Candida keroseneae, Acetobacter, Campylobacter jejuni, E. coli, Heliobacter pylori, Legionella pneumophila, Mycobacterium avium, Salmonella enterica, Shigella sonnei*, Adenovirus, Caliciviruses, *Enterovirus*, and Hepatitis A.

12. The fluid cleaning system of claim 11, wherein said contaminant capture manifold comprises a contaminant capture element for each of said one or more arrays, each said contaminate capture element comprising said polymerized receptor.

13. A system for removing biological contaminants from a fluid comprising:
one or more pairs of microelectromechanical sensors enclosed in a housing, each said pair comprised of one reference sensor and one detection sensor, said detection sensor comprising a receptor selected from a plurality of receptors, said receptor having an affinity for a biological contaminant in said fluid; and
one or more capture elements enclosed in a manifold corresponding to said one or more pairs of sensors, said manifold being in downstream fluid communication with said said housing, each said capture element comprising one of a spiral ramp comprising said receptor, a cylindrical wall coaled with said receptor, and a plurality of microbeads comprised of said receptor.

14. The system of claim 13, wherein said receptor has an affinity with at least one of *Hormoconis resinae, Micrococcus, Pseudomonas, Arthrobacter, Aspergillus, Fusarium, Penicillum, Candida keroseneae, Acetobacter, Campylobacter jejuni, E. coli, Heliobacter pylori, Legionella pneumophila, Mycobacterium avium, Salmonella enterica, Shigella sonnei*, Adenovirus, Caliciviruses, *Enterovirus*, and Hepatitis A.

15. The system of claim 14, wherein said one or more capture elements are disposable cartridges.

16. A system for detecting biological analytes in fluid comprising:
a detector module comprised of:
an array of microelectromechanical sensors comprised of at least one reference sensor and at least one detection sensor, said at least one detection sensor having a receptor selected from a plurality of receptors, said receptor having an affinity for a biological analyte in said fluid and configured to generate a detection signal representing detection of said biological analyte; and
a computer-based microprocessor responsive to said detection signal that is configured with a radio frequency communications module responsive to said microprocessor for transmitting said detection signal; and
a remote computer-based communications device responsive to said radio frequency communications module.

17. The system of claim 16, wherein said biological analyte is at least one of a bacterium, a virus, an enzyme and a protein.

18. The system of claim 16, wherein said detector module is disposed in one of a handheld probe and a fluid coupler.

19. The system of claim 18, wherein said biological analyte is at least one of a bacterium, a virus, an enzyme and a protein.

20. The system of claim 19, wherein said biological analyte is at least one of a bacterium and a virus, and wherein system further comprises one or more capture elements for removing said bacteria or said virus from said fluid, said one or more capture elements comprising said receptor.

21. The system of claim 16, wherein said array is one or more arrays comprised of a plurality of pairs of microcantilever sensors, each of said arrays comprising a plurality of said detection microcantilever sensors to detect one of said one or more of said biological analytes.

22. The system of claim 21, wherein said one or more biological analytes comprises at least one of a bacteria, a virus, an enzyme and a protein.

23. The system of claim 22, wherein said detector module is disposed in one of a handheld probe and a fluid coupler.

24. The system of claim 23, wherein said biological analyte is at least one of a bacterium and a virus, and wherein system further comprises one or more capture elements for removing said biological analyte from said fluid, said one or more capture elements comprising said receptor.

* * * * *